(12) United States Patent
Niwayama

(10) Patent No.: US 8,369,914 B2
(45) Date of Patent: Feb. 5, 2013

(54) OPTICAL MEASURING APPARATUS, OPTICAL MEASURING METHOD, AND STORAGE MEDIUM THAT STORES OPTICAL MEASURING PROGRAM

(75) Inventor: Masatsugu Niwayama, Hamamatsu (JP)

(73) Assignee: National University Corporation Shizuoka University, Shizuoka-shi (JP)

( * ) Notice: Subject to any disclaimer, the term of this patent is extended or adjusted under 35 U.S.C. 154(b) by 1100 days.

(21) Appl. No.: 12/303,040

(22) PCT Filed: May 31, 2007

(86) PCT No.: PCT/JP2007/061108
§ 371 (c)(1),
(2), (4) Date: Dec. 1, 2008

(87) PCT Pub. No.: WO2007/139192
PCT Pub. Date: Dec. 6, 2007

(65) Prior Publication Data
US 2009/0209836 A1    Aug. 20, 2009

(30) Foreign Application Priority Data
May 31, 2006    (JP) .................................. 2006-152177

(51) Int. Cl.
*A61B 5/00* (2006.01)
*A61B 6/00* (2006.01)
(52) U.S. Cl. ......... 600/323; 600/322; 600/473; 600/476
(58) Field of Classification Search .......... 600/322–324, 600/326, 328, 331, 473, 475, 476, 477
See application file for complete search history.

(56) References Cited

U.S. PATENT DOCUMENTS
5,524,617 A    6/1996 Mannheimer
6,280,381 B1 *  8/2001 Malin et al. ................... 600/322
(Continued)

FOREIGN PATENT DOCUMENTS
JP    5-317295    12/1993
JP    8-322821    12/1996
(Continued)

OTHER PUBLICATIONS

Maegawa et al., "Influence of Overlying Tissues on Muscle Oxygenation Measurement Using Spatially Resolved Near-Infrared Spectroscopy," *Technical Rport of the Institute of Electronics Information Communication Engineers*, 100(163):39-44 (2000).

(Continued)

*Primary Examiner* — Rene Towa
*Assistant Examiner* — Megan Leedy
(74) *Attorney, Agent, or Firm* — Marshall, Gerstein & Borun LLP

(57) ABSTRACT

The present invention provides an optical measuring apparatus and an optical measuring method for being able to correct the influence of a superficial tissue to be able to accurately measure a degree of light absorption of a deep layer tissue such as a human body and fruits, and a storage medium that stores an optical measuring program. The optical measuring apparatus includes a probe, and the probe includes one light emitting diode and two photodiodes. In a configuration of the optical measuring apparatus, one of the photodiodes receives light which is emitted from the light emitting diode and transmitted through a superficial layer and a deep layer of a tissue, and the other photodiode receives light having a deep layer transmission distance different from that of the light received by one of the photodiodes. The light received by the other photodiode is also transmitted through the superficial layer and deep layer of the tissue. Based on intensity of the light received by each photodiode, a control unit computes a propagation constant in a medium through which the light propagates. An arithmetic expression is selected in accordance with an input fat thickness of the tissue, and an absorption coefficient of the light from a muscle tissue using the arithmetic expression based on the fat thickness and a spatial slope. A hemoglobin concentration and an oxygen saturation are obtained based on the obtained absorption coefficient of the light.

8 Claims, 12 Drawing Sheets

U.S. PATENT DOCUMENTS

| | | |
|---|---|---|
| 6,597,931 B1 | 7/2003 | Cheng et al. |
| 6,662,031 B1 | 12/2003 | Khalil et al. .................. 600/322 |
| 7,043,287 B1 | 5/2006 | Khalil et al. .................. 600/310 |
| 2003/0166997 A1 | 9/2003 | Chance et al. ................. 600/322 |

FOREIGN PATENT DOCUMENTS

| | | |
|---|---|---|
| JP | 11-501848 | 2/1999 |
| JP | 2004-534934 | 11/2004 |
| WO | WO-98/23916 | 6/1998 |
| WO | WO-2004/110273 | 12/2004 |

OTHER PUBLICATIONS

Official action for Japanese Application No. 2008-517985, dated Dec. 6, 2011.

Supplementary European Search Report for Application No. 07744496, dated Jun. 23, 2009.

Fabbri, et al. "Optical measurements of absorption changes in two-layered diffusive media," Phys. Med. Biol. 49:1183-1201 (2004).

Kienle, et al. "Noninvasive determination of the optical properties of two-layered turbid media," Appl. Opt. 37:779-791 (1998).

Matcher, et al. "Performance Comparison of Several Published Tissue Near-Infrared Spectroscopy Algorithms," Anal. Biochem. 227:54-68 (1995).

Mitic et al. "Time-gated transillumination of biological tissues and tissue like phantoms," Appl Opt. 33:6699-6710 (1994).

Niwayama, et al. "Quantitative measurement of muscle hemoglobin oxygenation using near-infrared spectroscopy with correction for the influence of a subcutaneous fat layer," Rev. Sci. Instrum, 71:4571-4575 (2000).

Shimada, et al. "Simple algorithm for the measurement of absorption coefficients of a two-layered medium by spatially resolved and time-resolved reflectance," Appl. Opt. 44:7554-63 (2003).

van der Zee, et al. "Simulation of the point spread function for light in tissue by a Monte Carlo method," Adv. Exp. Med. Biol. 215:179-191 (1987).

Wan et al. "Analytical modeling for the optical properties of skin with in vitro and in vivo applications," Photochem Photobiol. 34:493-499 (1981).

Yamamoto, et al. "Accurate NIRS measurement of muscle oxygenation by correcting the influence of a subcutaneous fat layer," Proc SPIE, 3194:166-173 (1998).

Zaccanti, et al. "Optical properties of biological tissues," Proc. SPIE 2389:513-521 (1995).

* cited by examiner

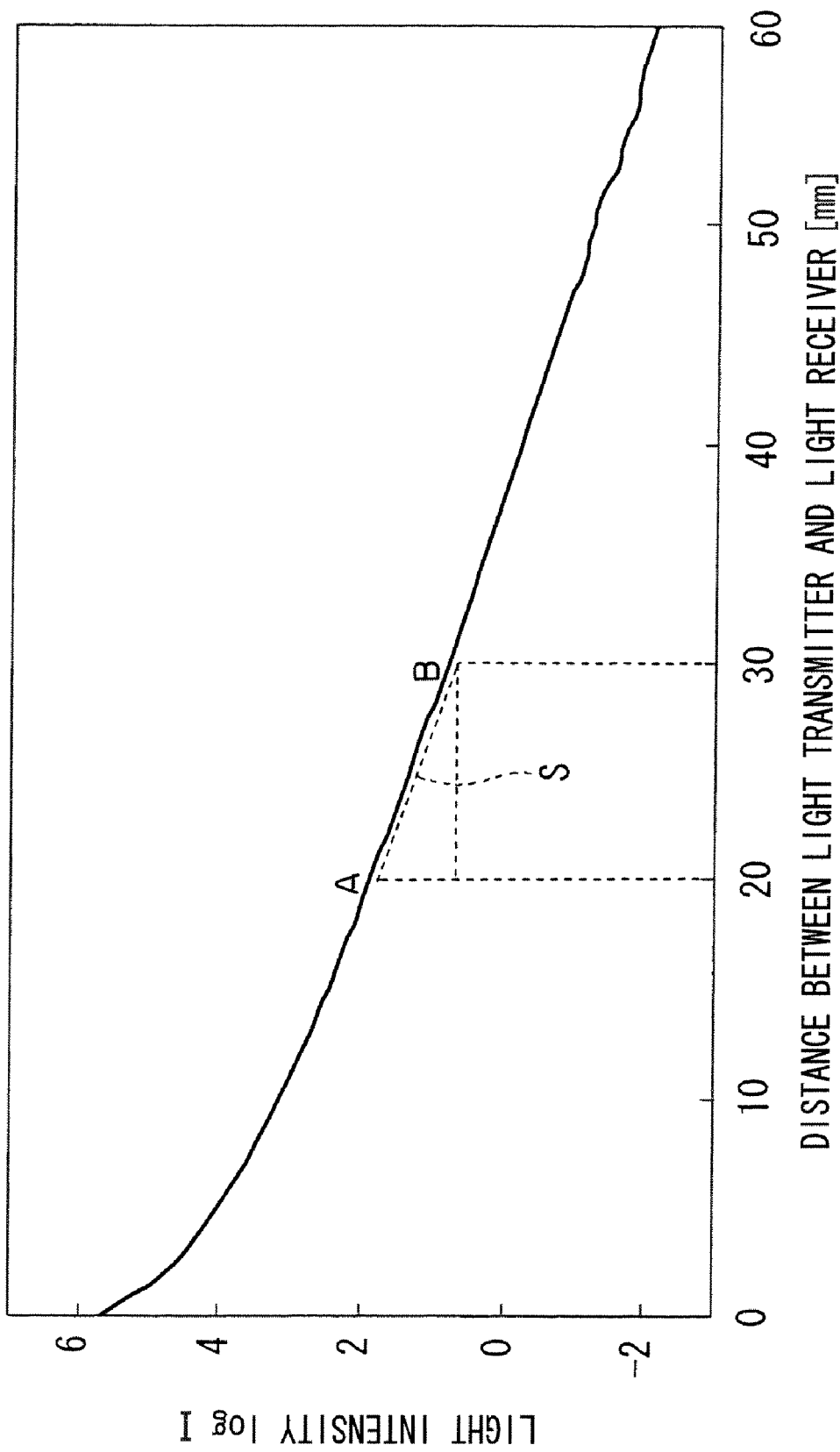

OPTICAL MEASURING APPARATUS, OPTICAL MEASURING METHOD, AND STORAGE MEDIUM THAT STORES OPTICAL MEASURING PROGRAM

TECHNICAL FIELD

The present invention relates to an optical measuring apparatus, an optical measuring method, and a storage medium that stores an optical measuring program, particularly to an optical measuring apparatus and an optical measuring method for measuring a degree of light absorption of a deep layer tissue such as a human body and fruits, and a storage medium that stores an optical measuring program.

BACKGROUND ART

Near-InfraRed Spectroscopy (NIRS) is an extremely useful technique of evaluating tissue metabolism, and NIRS is also applied in clinical practice. There is known a technique in which a living body such as a human body is irradiated with near-infrared light and a reflected light transmitted trough the living body is analyzed to measure a change in amount of blood in the living body. The measuring technique is based on a technique of utilizing a difference in light absorption characteristic between oxygenation and deoxygenation of the hemoglobin to detect a blood distribution state, thereby detecting a hemoglobin existing state.

Examples of NIRS include a continuous light method, a time resolved method, spatially resolved method, and an intensity modulation method. In each technique, when the deep layer tissue such as a muscle tissue and a brain is measured, a superficial tissue such as fat has a large influence on quantitative performance. The living body is usually formed by plural tissues, and the tissues have different absorption characteristics for the near-infrared light. Therefore, the analytical result of the reflected light includes information on the plural tissues.

The continuous light method and the spatially resolved method can be realized with a simple apparatus, and the continuous light method and the spatially resolved method have advantages in general versatility, portability, and real-time performance than any other methods. However, although a method for correcting an influence of a fat layer is proposed in NIRS in which the continuous light method is adopted (for example, see Non-Patent Documents 1 and 2), a method for correcting the influence of the superficial tissue is not sufficiently established yet in the spatially resolved method.

Although some investigations describe estimation of an absorption coefficient from a spatially resolved profile (for example, see Non-Patent Documents 3 to 5), there is shown no specific correction method which can easily be utilized for actual measurement of muscle tissue oxygen concentration. In addition to an error of absolute amount of hemoglobin concentration, it is also necessary to clarify an error in computing an oxygen saturation. Other investigation results are also reported (for example, see Non-Patent Documents 6 to 10).

Non-Patent Document 1: Yamamoto K, Niwayama M, Shiga T et al: Accurate NIRS measurement of muscle oxygenation by correcting the influence of a subcutaneous fat layer. Proc SPIE, 1998, 3194: 166-173.

Non-Patent Document 2: Niwayama M, Lin L, Shao J et al: Quantitative measurement of muscle hemoglobin oxygenation using near-infrared spectroscopy with correction for the influence of a subcutaneous fat layer. Rev Sci Instrum, 2000, 71: 4571-4575.

Non-Patent Document 3: Kienle A, Patterson M S, Dognitz N et al: Noninvasive determination of the optical properties of two-layered turbid media. Appl Opt, 1998, 37: 779-791.

Non-Patent Document 4: Fabbri F, Sassaroli A, Henry M E et al: Optical measurements of absorption changes in two-layered diffusive media. Phys Med Biol, 2004, 49: 1183-1201.

Non-Patent Document 5: Shimada M, Hoshi Y, Yamada Y: Simple algorithm for the measurement of absorption coefficients of a two-layered medium by spatially resolved and time-resolved reflectance. 2005, Appl Opt, 44: 7554-63.

Non-Patent Document 6: van der Zee P, Delpy D T: Simulation of the point spread function for light in tissue by a Monte Carlo method. Adv Exp Med Biol, 1987, 215: 179-191.

Non-Patent Document 7: Wan S, Anderson R R, Parrish J A: Analytical modeling for the optical properties of skin with in vitro and in vivo applications. Photochem Photobiol, 1981, 34: 493-499.

Non-Patent Document 8: Mitic G, Kozer J, Otto J et al: Time-gated transillumination of biological tissues and tissue like phantoms. 1994, Appl Opt, 33: 6699-6710.

Non-Patent Document 9: Zaccanti G, Taddeucci A, Barilli M et al: Optical properties of biological tissues. 1995, Proc. SPIE, 2389: 513-521.

Non-Patent Document 10: Matcher S J, Elwell C E, Cooper C E et al: Performance Comparison of Several Published Tissue Near-Infrared Spectroscopy Algorithms. Anal Biochem, 1995, 227: 54-68.

DISCLOSURE OF THE INVENTION

In view of the foregoing, an object of the invention is to obtain an optical measuring apparatus, an optical measuring method and an optical measuring program for being able to correct the influence of the superficial tissue to accurately measure the degree of light absorption of the deep layer tissue such as the human body and fruits, and a storage medium that stores an optical measuring program.

An aspect of the invention provides an optical measuring apparatus including a light emitting means for irradiating with light a layered structure which is an object of measurement, the layered structure including plural layers, the plural layers including at least a superficial layer and a deep layer; a light receiving means for receiving, at a position at a first predetermined distance from the light emitting means, light emitted from the light emitting means and transmitted through the superficial layer and the deep layer, and for receiving, at a position at a second predetermined distance from the light emitting means, light which is emitted from the light emitting means and transmitted through the superficial layer and the deep layer and which has a deep layer transmission distance which is different from that of the light received at the position at the first predetermined distance from the light emitting means; a spatial slope computation means for obtaining a spatial slope based on intensities of the light received at the position at the first predetermined distance from the light emitting means and the light received at the position at the second predetermined distance from the light emitting means; a storage means in which a computation parameter for computing a degree of light absorption in the deep layer are stored for each superficial thickness; an input means for inputting the superficial thickness; and a computing means for reading the computation parameter from the storage means in accordance with the input superficial thickness, and obtaining the degree of light absorption based on the read computation parameter and the spatial slope.

The light emitting means irradiates with light the layered structure which is the object of measurement. The light receiving means receives light transmitted through the superficial layer and deep layer in the light emitted from the light emitting means at the position at the first predetermined distance from the light emitting means, and the light receiving means also receives light at the position at the second predetermined distance from the light emitting means in the light emitted from the light emitting means. The light received at the position at the second predetermined distance from the light emitting means is transmitted through the superficial layer and deep layer, and the light has the deep layer transmission distance different from that of the light received at the position at the first predetermined distance from the light emitting means.

In another aspect of the invention, the light receiving means includes a first light receiving unit at the first predetermined distance from the light emitting means; and a second light receiving unit at the second predetermined distance from the light emitting means.

The spatial slope computation means obtains the spatial slope based on the intensities of the light received at the position at the first predetermined distance from the light emitting means and the light received at the position at the second predetermined distance from the light emitting means.

The computation parameters for computing the degree of light absorption in the deep layer of the layered media of the object of measurement are stored for each superficial thickness in the storage means. The computation parameter may be an arithmetic expression or a parameter (coefficient) for specifying the arithmetic expression.

The computing means reads the computation parameter from the storage means in accordance with the superficial thickness of the layered structure of the object of measurement, and the computing means obtains the degree of light absorption based on the read computation parameter and the spatial slope computed by the spatial slope computation means. The superficial thickness of the layered structure of the object of measurement is input by the input means.

Thus, using the computation parameter selected in accordance with the superficial thickness of the layered structure of the object of measurement, the degree of light absorption of the deep layer of the layered structure is measured, so that the influence of the superficial layer of the layered structure can be corrected to accurately measure the degree of light absorption.

In another aspect of the invention, the layered structure is a part of a living body, the superficial layer is a fat tissue, and the deep layer is a muscle tissue.

In this case, in another aspect of the invention, the computing means can further obtain the oxygenated hemoglobin concentration, the deoxygenated hemoglobin concentration, and an oxygen saturation, based on the degree of light absorption. Therefore, the optical measuring apparatus according to the aspect of the invention can be applied to a practice load monitor in rehabilitation or training.

In another aspect of the invention, the light receiving means includes a first light receiving unit at the first predetermined distance from the light emitting means; and a second light receiving unit at the second predetermined distance from the light emitting means.

Another aspect of the invention provides an optical measuring method including irradiating with light a layered structure which is an object of measurement, the layered structure including plural layers, the plural layers including at least a superficial layer and a deep layer; receiving, at a position at a first predetermined distance from a light irradiation position, light of the irradiation light which has been transmitted through the superficial layer and the deep layer, and receiving, at a position at a second predetermined distance from the light irradiation position, light of the irradiation light which has been transmitted through the superficial layer and the deep layer and which has a deep layer transmission distance which is different from that of the light received at the position at the first predetermined distance from the light irradiation position; obtaining a spatial slope based on intensities of the light received at the position at the first predetermined distance from the light irradiation position, the light received at the position at the second predetermined distance from the light irradiation position, the first predetermined distance, and the second predetermined distance; inputting the superficial thickness; and reading a computation parameter from a storage means in accordance with the input superficial thickness, where the computation parameters for computing a degree of light absorption in the deep layer are stored for each superficial thickness in the storage means, and obtaining the degree of light absorption based on the read computation parameter and the spatial slope.

Thus, using the computation parameter selected in accordance with the superficial thickness of the layered structure of the object of measurement, the degree of light absorption of the deep layer of the layered structure is measured, so that the influence of the superficial layer of the layered structure can be corrected to accurately measure the degree of light absorption.

Another aspect of the invention provides a storage medium that stores an optical measuring program for causing a computer to executes processing, the processing including, a step of irradiating with light a layered structure which is an object of measurement, the layered structure including plural layers, the plural layers including at least a superficial layer and a deep layer; a step of receiving, at a position at a first predetermined distance from a light irradiation position, light of the irradiation light which has been transmitted through the superficial layer and the deep layer, and receiving, at a position at a second predetermined distance from the light irradiation position, light of the irradiation light which has been transmitted through the superficial layer and the deep layer, and which has a deep layer transmission distance which is different from that of the light received at the position at the first predetermined distance from the light irradiation position; a step of obtaining a spatial slope based on intensities of the light received at the position at the first predetermined distance from the light irradiation position, the light received at the position at the second predetermined distance from the light irradiation position, the first predetermined distance, and the second predetermined distance; a step of inputting the superficial thickness; and a step of reading a computation parameter from a storage means in accordance with the input superficial thickness, where the computation parameters for computing a degree of light absorption in the deep layer are stored for each superficial thickness in the storage means, and obtaining the degree of light absorption based on the read computation parameter and the spatial slope.

Thus, using the computation parameter selected in accordance with the superficial thickness of the layered structure of the object of measurement, the degree of light absorption of the deep layer of the layered structure is measured, so that the influence of the superficial layer of the layered structure can be corrected to accurately measure the degree of light absorption.

According to the invention, advantageously the influence of the superficial layer can be corrected to accurately measure the degree of light absorption of the deep layer tissue such as the human body and fruits.

BRIEF DESCRIPTION OF THE DRAWINGS

FIG. 3 is a diagrammatic view showing a relationship between a distance between a light transmitter and a light receiver and a spatial slope S.

Figure 1:
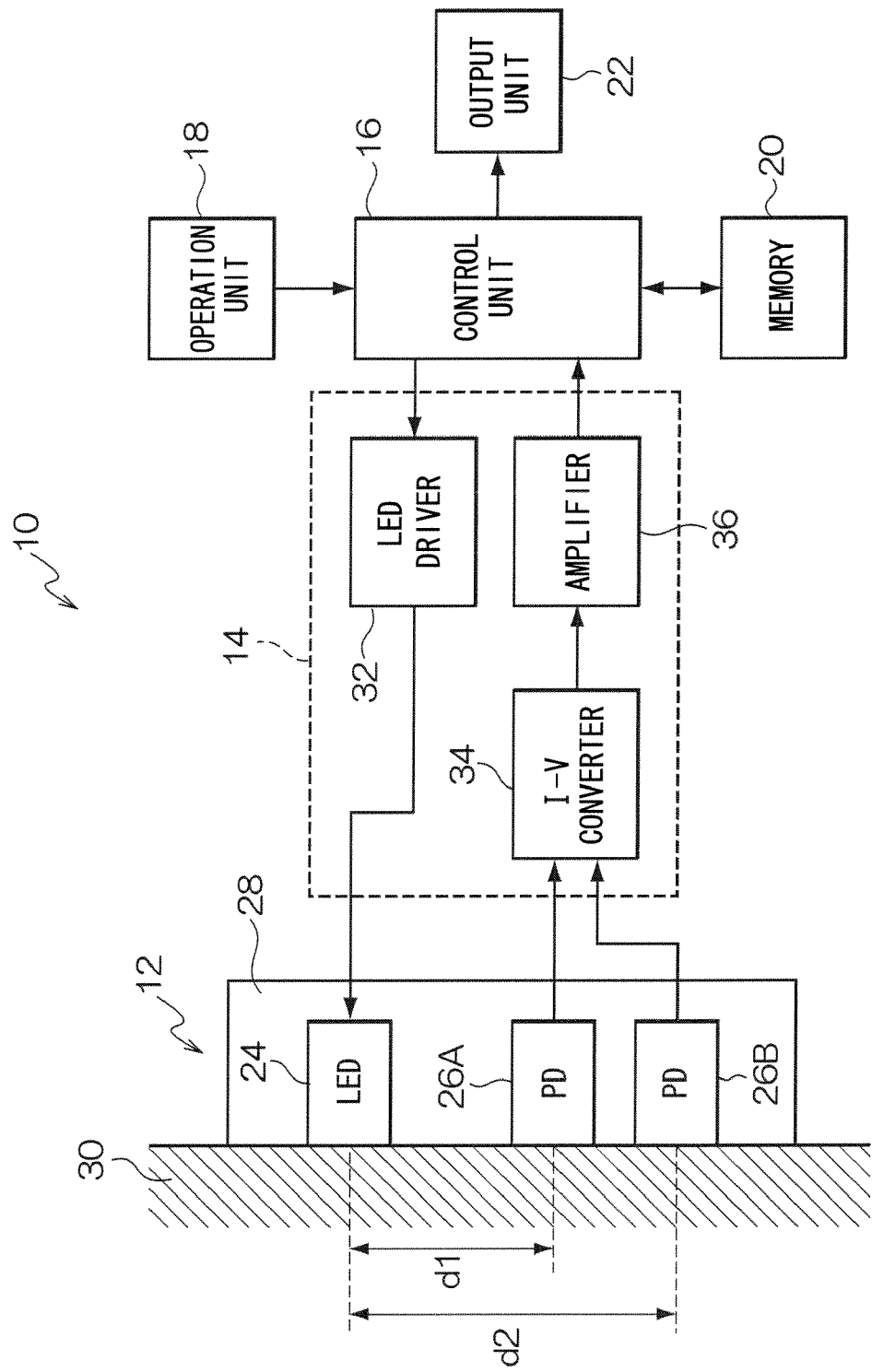
FIG. 1 is a schematic diagram of an optical measuring apparatus.

DESCRIPTION OF REFERENCE NUMERALS 10 optical measuring apparatus
12 probe
14 driving device
16 control unit (spatial slope computation means, computing means)
18 operation unit (input means)
20 memory (storage means)
22 output unit
24 LED (light emitting means)
26A PD (first light receiving unit)
26B PD (second light receiving unit)
30 tissue
32 LED driver
34 I-V converter
36 amplifier

BEST MODE FOR CARRYING OUT THE INVENTION

An exemplary embodiment of the present invention will be described with reference to the drawings.

In the exemplary embodiment, the case in which an amount of blood in a muscle tissue of a human arm, that is, a hemoglobin concentration or an oxygen saturation is measured will be described by way of example.

FIG. 1 shows a schematic configuration of an optical measuring apparatus 10. Referring to FIG. 1, the optical measuring apparatus 10 includes a probe 12, a driving device 14, a control unit 16, an operation unit 18, a memory 20, and an output unit 22.

In the probe 12, LED (Light Emitting Diode) 24 and two PDs (PhotoDiodes) 26A and 26B are provided in a flexible planar member (such as rubber member) 28. The probe 12 is brought into contact with an arm of a subject in order to irradiate an inside of a tissue 30 with light in the arm of the subject.

In the exemplary embodiment, a light emitting diode is used as LED 24 by way of example. The light emitting diode has two peak wavelengths, that is, a first wavelength $\lambda 1$ and a second wavelength $\lambda 2$. The first wavelength $\lambda 1$ and the second wavelength $\lambda 2$ are set at a wavelength in which a small amount of water is absorbed. Specifically, the wavelengths are set at values of 900 nm or less, and the wavelengths are set at wavelengths located at an equal distance from about 805 nm. The wavelength of about 805 nm is a position at which absorption spectra of deoxygenated hemoglobin Hb and oxygenated hemoglobin $HbO_2$ intersect each other. In the exemplary embodiment, the first wavelength $\lambda 1$ is set at 770 nm, and the second wavelength $\lambda 2$ is set at 830 nm.

LED 24 and PD 26A are disposed by a first predetermined distance d1 from each other, and LED 24 and PD 26B are disposed by a second predetermined distance d2.

The first predetermined distance d1 is set at such a distance that the light emitted from LED 24 reaches PD 26A through the deep layer portion of the human arm, that is, the muscle tissue located below the skin tissue (surface layer) and the fat tissue (superficial layer). The inventor experimentally confirms that a general-purpose electronic circuit can detect the information on the deep layer with a sufficient S/N ratio when the light transmission distance (in this case, an average optical path length) is about 10 mm or more in the deep layer of the object of measurement. A distance between a light transmitter and a light receiver is obtained from a simulation such that the light transmission distance of the deep layer is 10 mm or more when a superficial thickness ranges from 0 to 8 mm. As a result of the simulation, in the exemplary embodiment, the first predetermined distance d1 is set at 20 mm by way of example.

The second predetermined distance d2 is set at such a distance that the light emitted from LED 24 reaches PD 26B through the deep layer portion of the human arm, and the distance that is different from the first predetermined distance. When the distance between light transmitter and light receiver becomes longer, the light intensity is attenuated in an exponential manner, and the general-purpose electronic circuit hardly detects the information on the deep layer. Therefore, the inventor obtains the distance between the light transmitter and the light receiver, where the general-purpose electronic circuit can detect the light intensity, from the theory and experiment. Accordingly, in the exemplary embodiment, the second predetermined distance d2 is set at 30 mm by way of example. The first predetermined distance d1 and the second predetermined distance d2 are set at 20 mm and 30 mm by way of example, and the first predetermined distance d1 and the second predetermined distance d2 are properly set in accordance with the depth to the muscle tissue to be measured.

The driving device 14 includes a LED driver 32, an I-V converter 34, and an amplifier 36.

In response to an instruction from the control unit 16, the LED driver 32 causes LED 24 to emit the light with a predetermined wavelength and a predetermined light intensity.

The I-V converter 34 converts a current which is obtained by photoelectric conversion of the light received by PDs 26A and 26B into a voltage, and the I-V converter 34 supplies the voltage to the amplifier 36.

The amplifier 36 amplifies the voltage converted by the I-V converter 34 to a predetermined level, and the amplifier 36 supplies the amplified voltage in the form of a signal indicating a light intensity to the control unit 16.

The control unit 16 provides an instruction to cause LED 24 to emit the light to the LED driver 32, and the control unit 16 computes a hemoglobin concentration from a later-mentioned operation based on the light intensities received by PDs 26A and 26B. The operation result is input into the output unit 22. For example, the output unit 22 includes a display or a printer, and the output unit 22 displays or prints the operational result.

A later-mentioned processing routine program and simulation result data used in the processing are previously stored in the memory 20.

Figure 2:
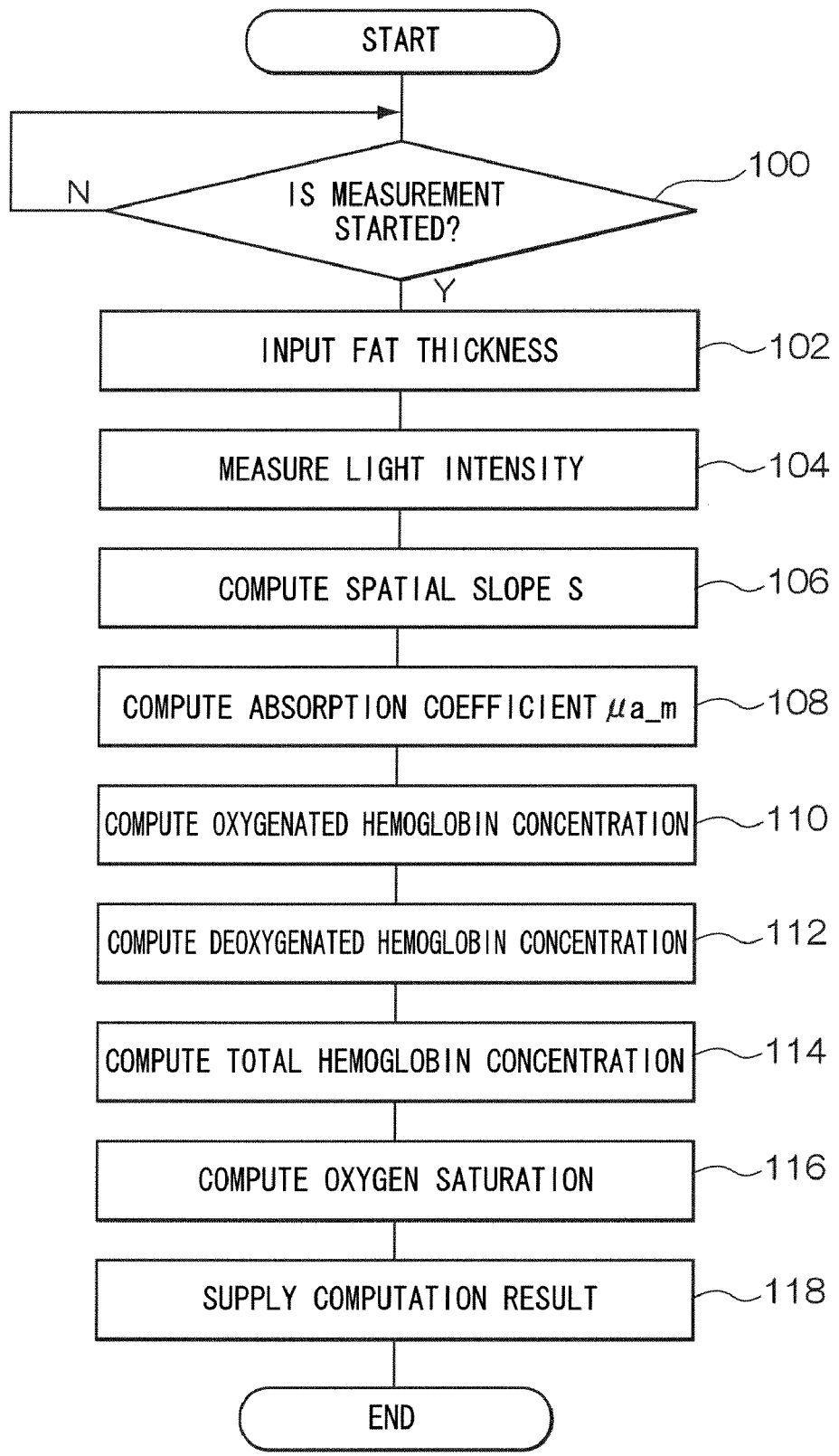
FIG. 2 is a flowchart showing processing performed by a control unit.

Then, measurement processing performed by the control unit 16 will be described as action of the exemplary embodiment with reference to a flowchart of FIG. 2. The measurement processing is performed once the optical measuring apparatus 10 is turned on.

In the measurement, the probe 12 is brought into contact with a subject arm, and the operation unit 18 is operated, thereby providing an instruction to start the measurement.

In Step 100, the control unit 16 determines whether or not the instruction to start the measurement is provided by the operation of the operation unit 18. When the instruction to start the measurement is provided, the flow goes to Step 102.

In Step 102, a fat thickness of the subject is input by the operation of the operation unit 18. For example, the fat thickness is measured with a simple measuring member such as a slide caliper, and the fat thickness is input. A fat thickness measuring apparatus (not shown) such as an ultrasonic diagnostic apparatus is connected to an optical measuring apparatus 10, and the fat thickness measured with the fat thickness measuring apparatus may directly be input. The input fat thickness is required in obtaining an absorption coefficient μa_m (degree of light absorption) of a muscle tissue mentioned later.

In Step 104, the control unit 16 provides the instruction to cause LED 24 to emit the light to the LED driver 32, and the control unit 16 takes in light intensities $I_A$ and $I_B$ received from PD 26A and PD 26B from the amplifier 36. The light is sequentially emitted at the first wavelength λ1 and the second wavelength λ2, and the light intensities $I_A$ and $I_B$ are taken in at each wavelength. In the following description, it is assumed that $I_{A1}$ and $I_{B1}$ are the light intensities received by PD 26A and PD 26B when the light is emitted at the first wavelength λ1 and it is assumed that that $I_{A2}$ and $I_{B2}$ are the light intensities received by PD 26A and PD 26B when the light is emitted at the second wavelength λ2.

In Step 106, the control unit 16 obtains a spatial slope S in the spatially resolved method based on the light intensities measured in Step 104. As shown in FIG. 3, there is a relationship of the distance between LED and PD (distance between the light transmitter and the light receiver) and the light intensity (logI). In the exemplary embodiment, the spatial slope S is expressed by a gradient of a line connecting a point A and a point B. The point A indicates the light intensity when the distance between the light transmitter and the light receiver is 20 mm, and the point B indicates the light intensity when the distance between the light transmitter and the light receiver is 30 mm. In the exemplary embodiment, for the sake of convenience, the spatial slope S is defined as follows.

[Formula 1]

$$S = \ln(I_A/I_B)/\rho \quad (1)$$

Here, ρ is the distance between PD 26A and PD 26B, and ρ becomes 10 mm because of the d1=20 mm and d2=30 mm in the exemplary embodiment.

The spatial slope S is obtained in each wavelength. In the following description, it is assumed that S1 is a spatial slope obtained based on the light intensities $I_{A1}$ and $I_{B1}$ when the light is emitted at the first wavelength λ1, and it is assumed that S2 is a spatial slope obtained based on the light intensities $I_{A2}$ and $I_{B2}$ when the light is emitted at the second wavelength λ2.

In Step 108, the control unit 16 obtains the absorption coefficient μa_m of the muscle tissue of the arm which is the object of measurement based on the spatial slope S1 and S2 obtained in Step 106. The absorption coefficient μa_m of the muscle tissue is obtained by using an S-μa_m curve derived from result of a later-mentioned Monte Carlo simulation.

The result of Monte Carlo simulation performed by the inventor will be described below. In order to realize the quantitative oxygen concentration of the muscle tissue, the inventor performed the Monte Carlo simulation using a three-layer model having skin, fat, and muscle tissues as a model of the living-body tissue. A general algorithm in which a group of photons is randomly walked in the model and an amount of the group of photons is attenuated in accordance with a kind of a medium passing the photons is used as a light propagation algorithm (see Non-Patent Document 6).

Thickness and optical constants (scattering coefficient and absorption coefficient) of the layers are set as shown in Table 1 (see Non-Patent Documents 7 to 9).

TABLE 1

| tissue | scattering coefficient μs (mm$^{-1}$) | absorption coefficient μa (mm$^{-1}$) | thickness |
|---|---|---|---|
| skin | 1.3 | 0.020 | 1.5 |
| fat | 1.2 | 0.002 | 0 to 15 |
| muscle | 0.8 | 0.020 | 200 |

In the simulation, the influence of the thickness was verified by changing the fat thickness, and the skin absorption coefficient and the scattering coefficient were increased and decreased by 20% to analyze the influence of the superficial layer and superficial tissues on the optical constants. In the spatially resolved method, it is necessary that the scattering coefficient μs_m of the muscle tissue be set at a value which is judged as proper. The case in which the scattering coefficient μs_m of the muscle tissue was increased and decreased by 0.2 mm$^{-1}$ was simulated to investigate an error when the judgment was different from the fact.

Figure 4A:
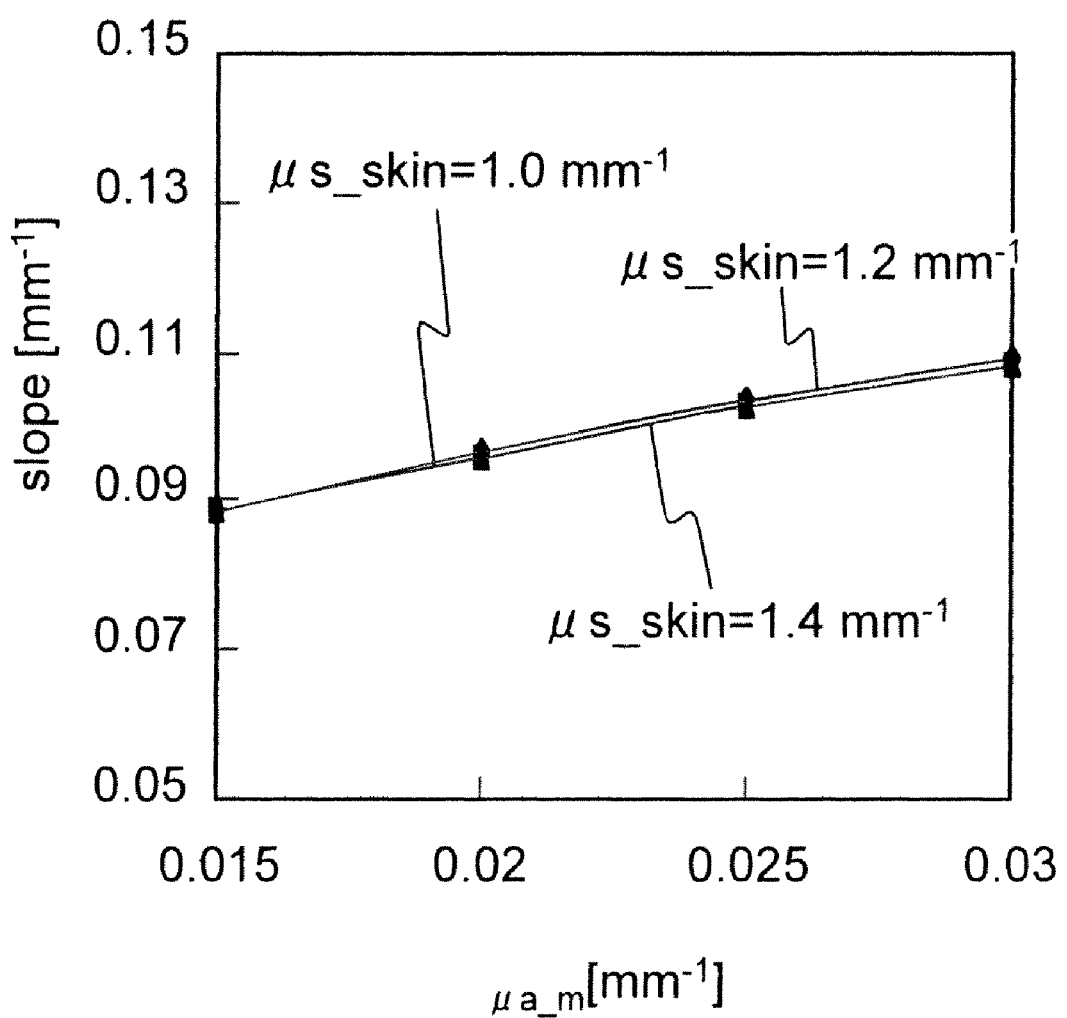
FIG. 4A is a diagrammatic view showing a relationship between an absorption coefficient of a muscle tissue and a spatial slope S in each skin absorption coefficient.
Figure 4B:
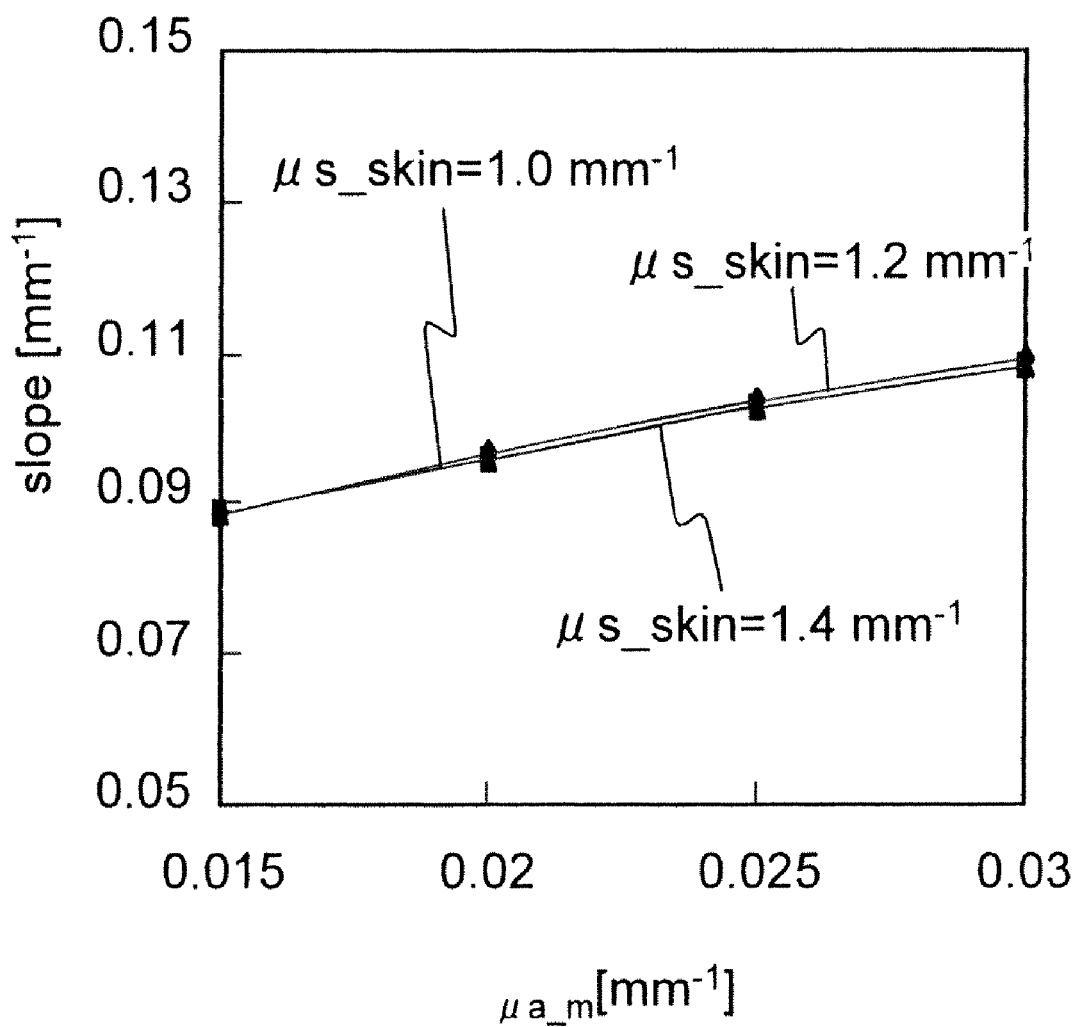
FIG. 4B is a diagrammatic view showing a relationship between an absorption coefficient of a muscle tissue and a spatial slope S in each skin scattering coefficient.

FIG. 4A shows the result of the relationship between the absorption coefficient μa_m of the muscle tissue and the spatial slope S (slope) when a skin absorption coefficient μa_mskin is 0.01 mm$^{-1}$, 0.0125 mm$^{-1}$, and 0.015 mm$^{-1}$, and FIG. 4B shows the result of the relationship between the absorption coefficient μa_m of the muscle tissue and the spatial slope S (slope) when a skin scattering coefficient μs_skin is 1.0 mm$^{-1}$, 1.2 mm$^{-1}$, and 1.4 mm$^{-1}$. As can be seen from FIGS. 4A and 4B, sometimes the skin absorption coefficient μa_skin and the scattering coefficient μs_skin have little influence on the absorption coefficient μa_m of the muscle tissue.

Figure 5A:
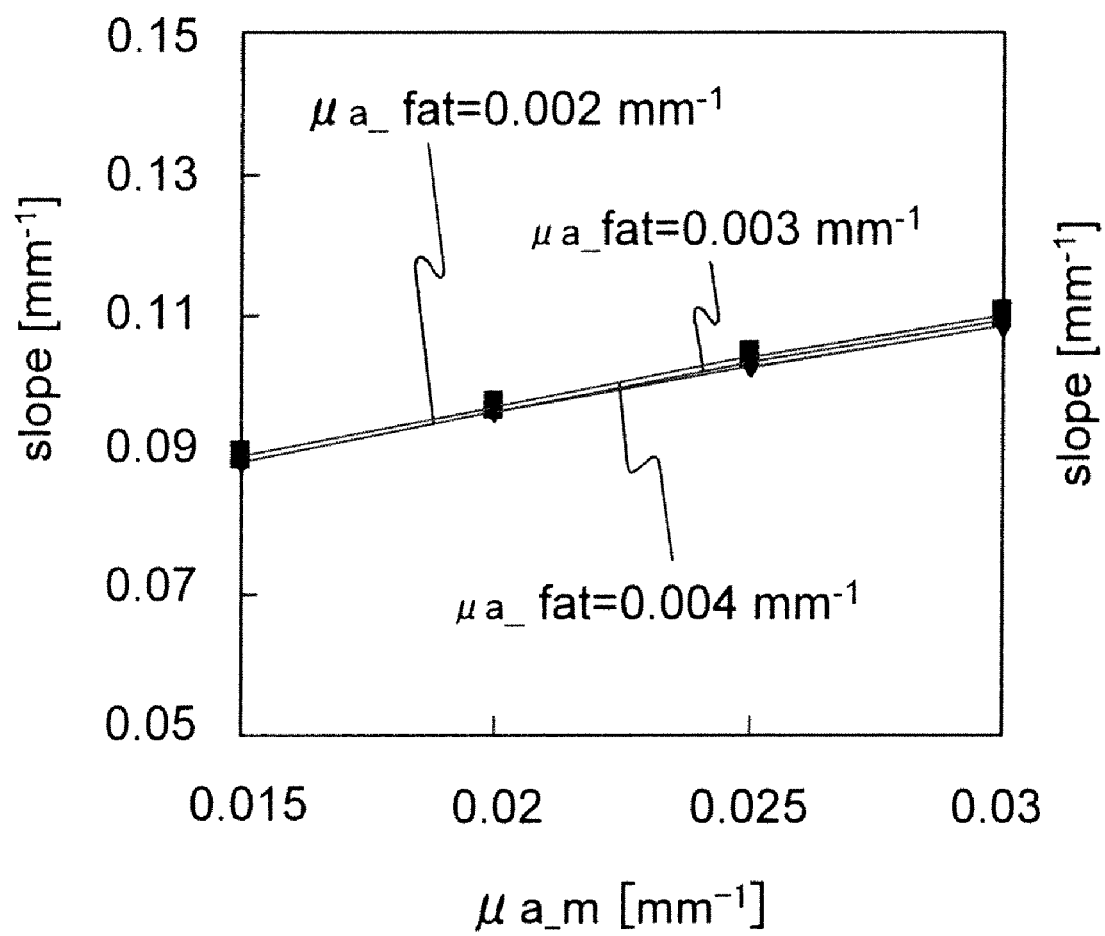
FIG. 5A is a diagrammatic view showing a relationship between an absorption coefficient of a muscle tissue and a spatial slope S in each fat absorption coefficient.
Figure 5B:
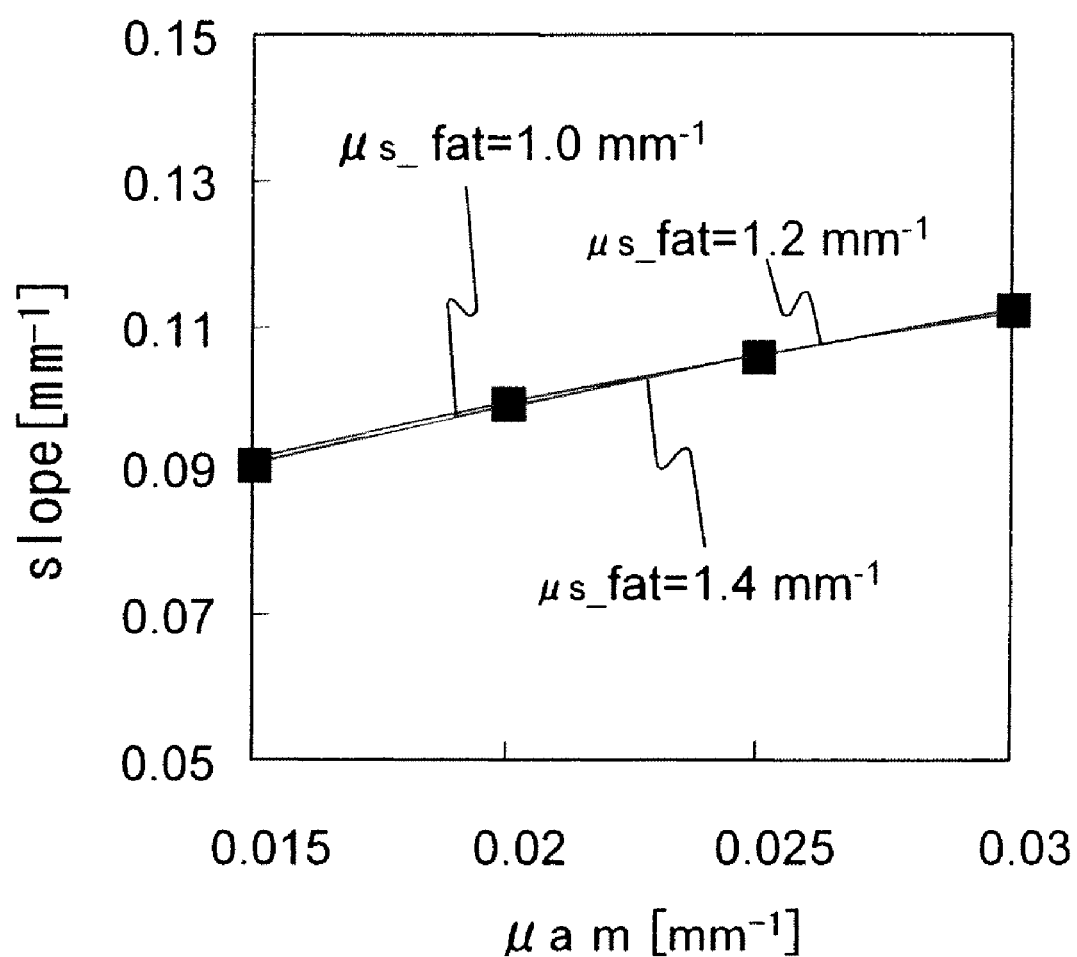
FIG. 5B is a diagrammatic view showing a relationship between an absorption coefficient of a muscle tissue and a spatial slope S in each fat scattering coefficient.

FIG. 5A shows the result of the relationship between the absorption coefficient μa_m of the muscle tissue and the spatial slope S (slope) when a fat absorption coefficient μa_fat is 0.002 mm$^{-1}$, 0.003 mm$^{-1}$, and 0.004 mm$^{-1}$, and FIG. 5B shows the result of the relationship between the absorption coefficient μa_m of the muscle tissue and the spatial slope S (slope) when a fat scattering coefficient μ_fat is 1.0 mm$^1$, 1.2 mm$^{-1}$, and 1.4 mm$^{-1}$. As can be seen from FIGS. 5A and 5B, sometimes the fat absorption coefficient μa_fat and the scattering coefficient μs_fat have little influence on the absorption coefficient μa_m of the muscle tissue.

Figure 6:
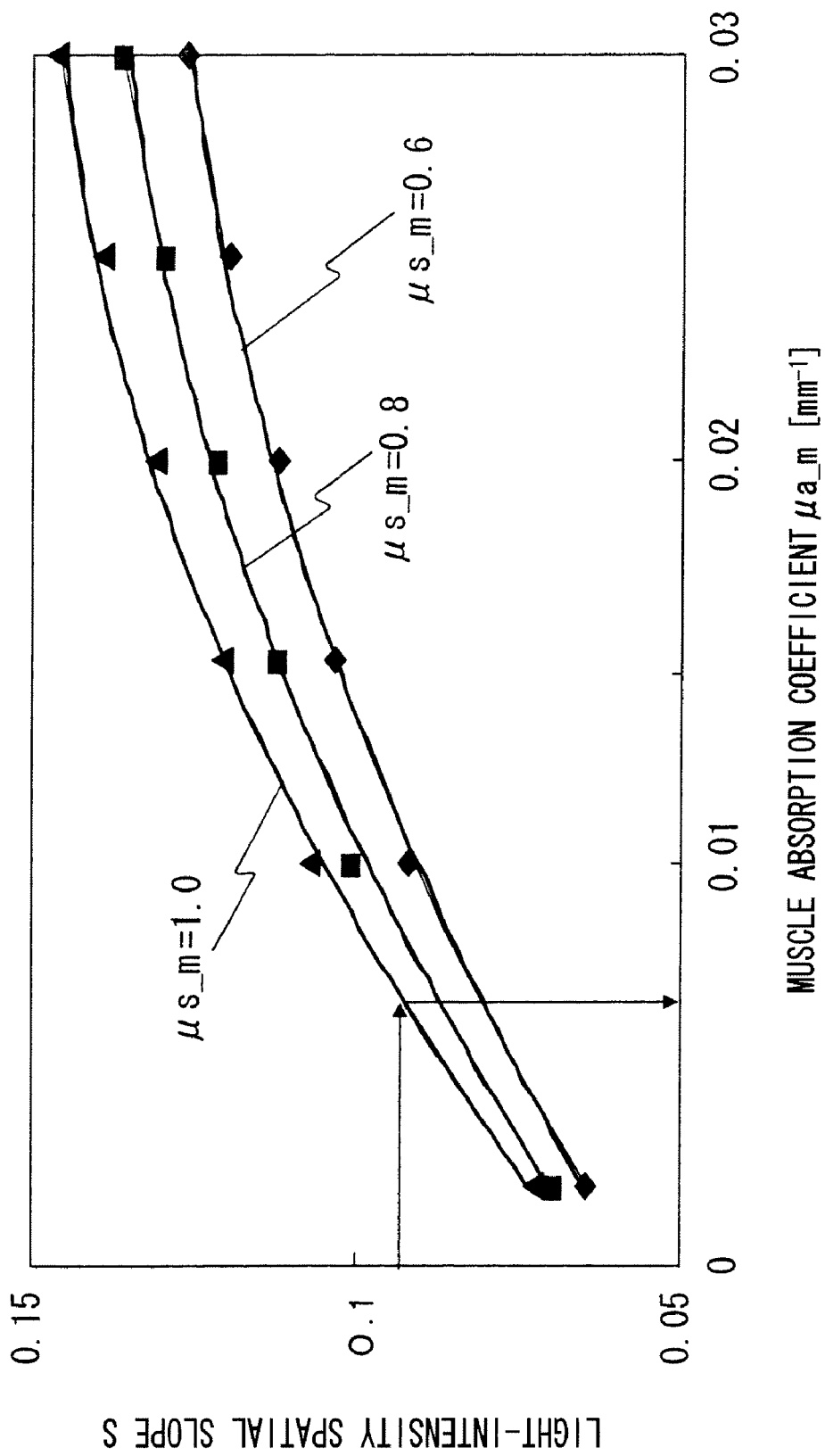
FIG. 6 is a diagrammatic view showing a relationship between an absorption coefficient of a muscle tissue and a spatial slope S in each absorption coefficient of the muscle tissue.

FIG. 6 shows the result of the relationship between the absorption coefficient μa_m of the muscle tissue and the spatial slope S when the scattering coefficient μs_m of the muscle tissue is 1.0 mm$^{-1}$, 0.8 mm$^{-1}$, and 0.6 mm$^{-1}$. As can be seen from FIG. 6, when the scattering coefficient μs_m of the muscle tissue is decreased by 0.2 mm$^1$, an absolute value of the absorption coefficient pa-m of the muscle tissue is increased by 20% or more.

Figure 7:
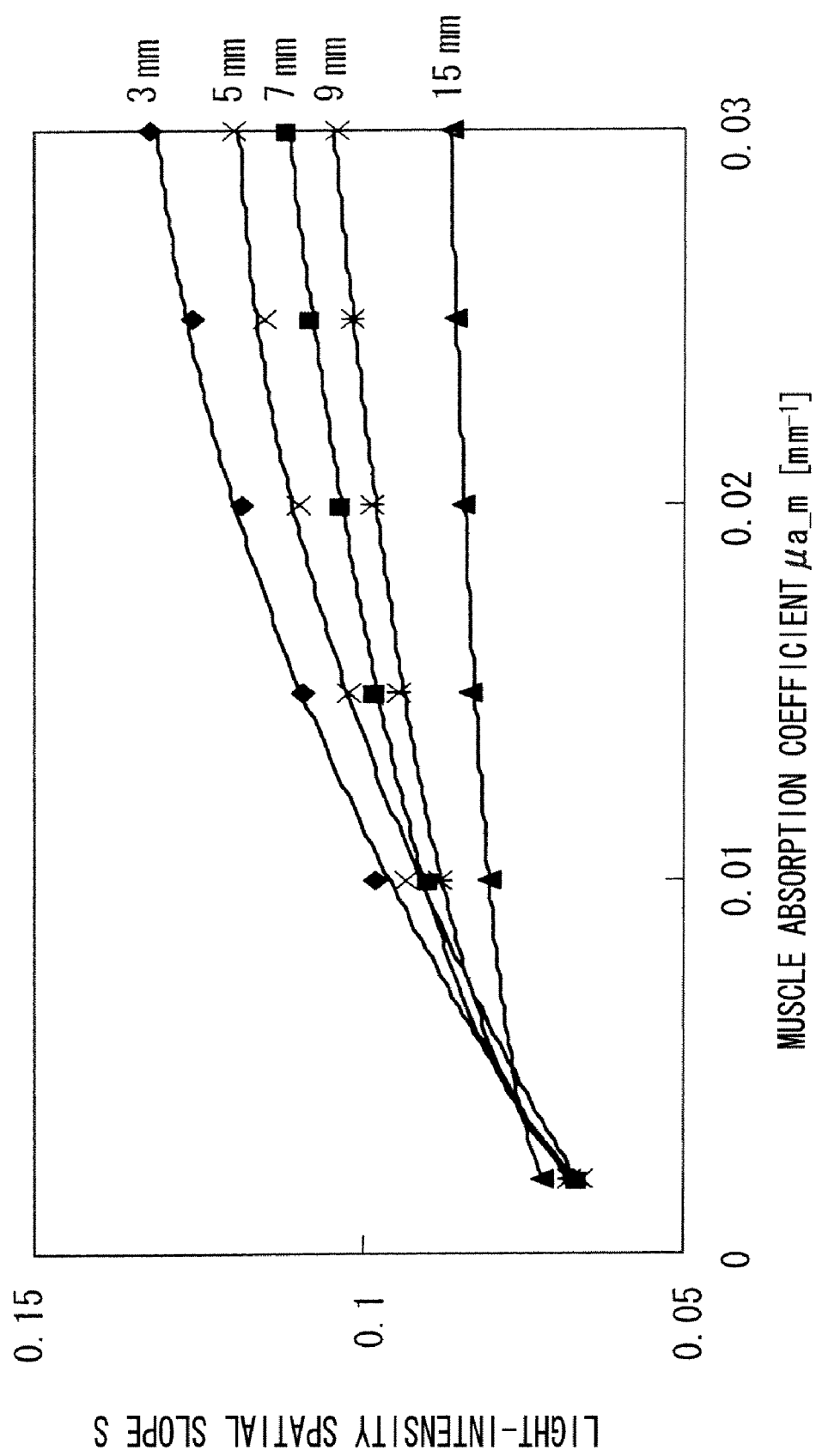
FIG. 7 is a diagrammatic view showing a relationship between an absorption coefficient of a muscle tissue and a spatial slope S in each fat thickness.

FIG. 7 shows the result of the relationship (S-μa_m curve) between the absorption coefficient μa_m of the muscle tissue and the spatial slope S when the fat thickness is 3, 5, 7, 9, and 15 mm. As can be seen from FIG. 7, a shape of the S-μa_m curve heavily depends on the fat thickness. Therefore, the fat thickness of the subject is previously measured, and the S-μa_m curve is used in accordance with the fat thickness, which allows the quantification of the absorption coefficient μa_m of the muscle tissue. The S-μa_m curve can be approximated by the following quadratic expression for the spatial slope S.

[Formula 2]

$$\mu_{a\_m} = aS^2 + bS + c \quad (2)$$

Here, a, b, and c are constant. The constants a, b, and c are obtained in each fat thickness and each wavelength from the result of the Monte Carlo simulation shown in FIG. 7, and the constants a, b, and c are previously stored in the memory 20. Therefore, the absorption coefficient μa_m can be obtained from the fat thickness and the spatial slope S. The constants a, b, and c depend on the fat thickness, the scattering coefficient μs_m of the muscle tissue, and the distance between the light transmitter and the light receiver. In the simulation performed by the inventor, for example, a=4.95, b=−0.56, and c=0.017 were obtained in the case of the fat thickness of 3 mm and the scattering coefficient μs_m of the muscle tissue is 0.8 mm$^{-1}$. When the skin absorption coefficient μa_skin and the skin scattering coefficient μs_skin were increased and decreased by 20%, the S-μa_m curve became substantially identical. Therefore, it is found that the optical constants for the skin have no influence in the spatially resolved method.

Figure 8:
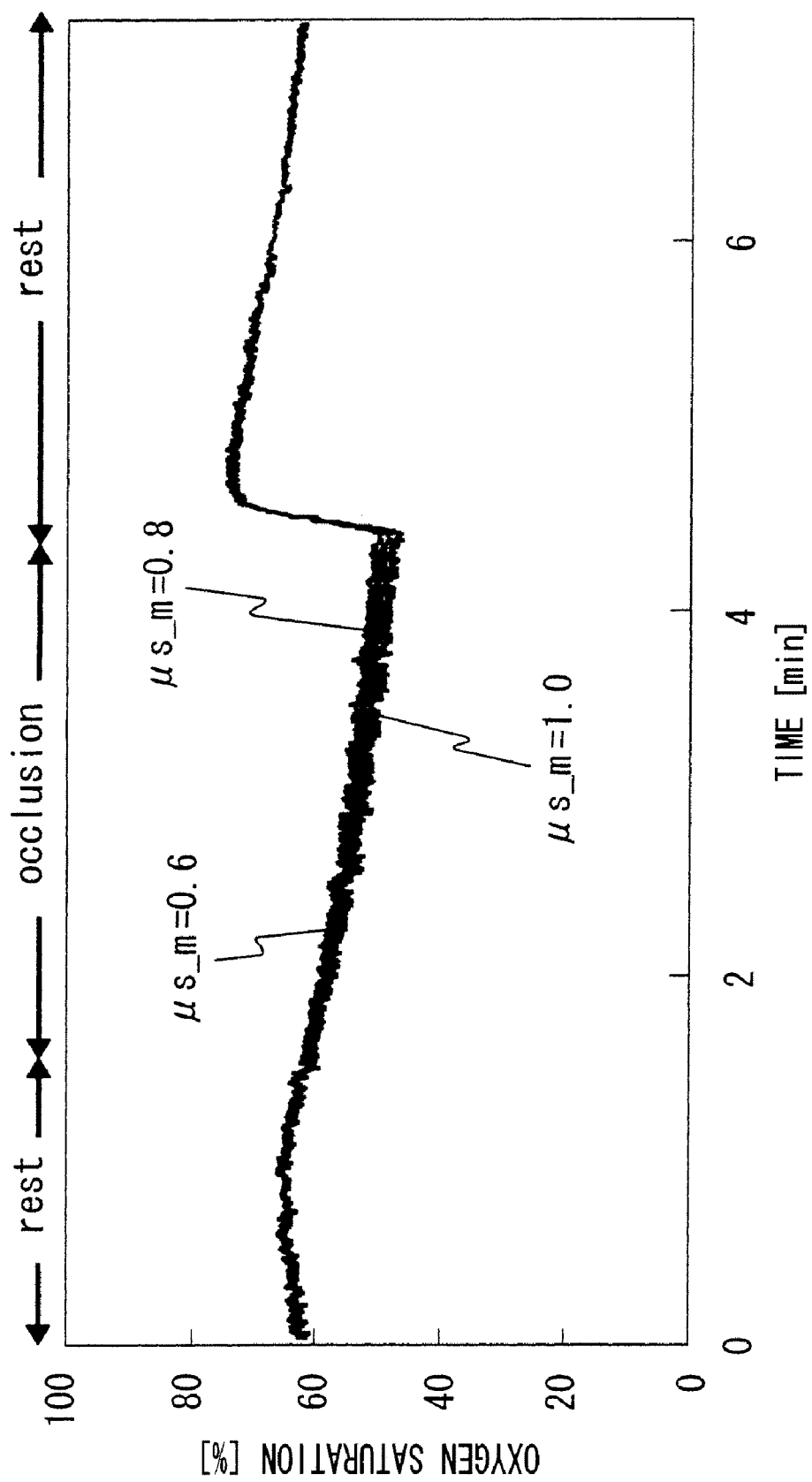
FIG. 8 is a diagrammatic view showing an oxygen saturation in each scattering coefficient of a muscle tissue.

FIG. 8 shows the result in which oxygen saturation $S_tO_2$ is actually measured when the scattering coefficient μs_m of the muscle tissue is 0.6 mm$^{-1}$, 0.8 mm$^{-1}$, and 1.0 mm$^{-1}$. As described later, the oxygen saturation is obtained by dividing the oxygenated hemoglobin concentration by the total hemoglobin concentration (sum of the oxygenated hemoglobin concentration and the deoxygenated hemoglobin concentration). In FIG. 8, an "occlusion" period is a period during which an artery and a vein are closed, that is a period during which a process for tightening up the upper arm to stop a blood flow, and a "rest" period is a period during which nothing is done.

As described above, the absolute value of the absorption coefficient pa-m of the muscle tissue is increased by 20% or more when the scattering coefficient μs_m of the muscle tissue is decreased by 0.2 mm$^{-1}$. However, as can be seen from FIG. 8, an error of the scattering coefficient μs_m of the muscle tissue falls within several percent for the oxygen saturation $S_tO_2$. This is attributed to that fact that a ratio of the two absorption coefficients is observed because the oxygen saturation $S_tO_2$ is expressed by a ratio of the oxygenated hemoglobin concentration to the total hemoglobin concentration. Even if the S-μa_m curve is changed by the scattering coefficient μs_m of the muscle tissue, when the S-μa_m curves have similarity, the ratio of the two absorption coefficients obtained from the S-μa_m curves becomes identical. The error of the oxygen saturation $S_tO_2$ is significantly small. This is attributed to that fact that a difference in scattering coefficient μs_m of the muscle tissue mainly has an influence on magnitude in a direction of a vertical axis of the S-μa_m curve while having little influence on the shape.

Figure 9:
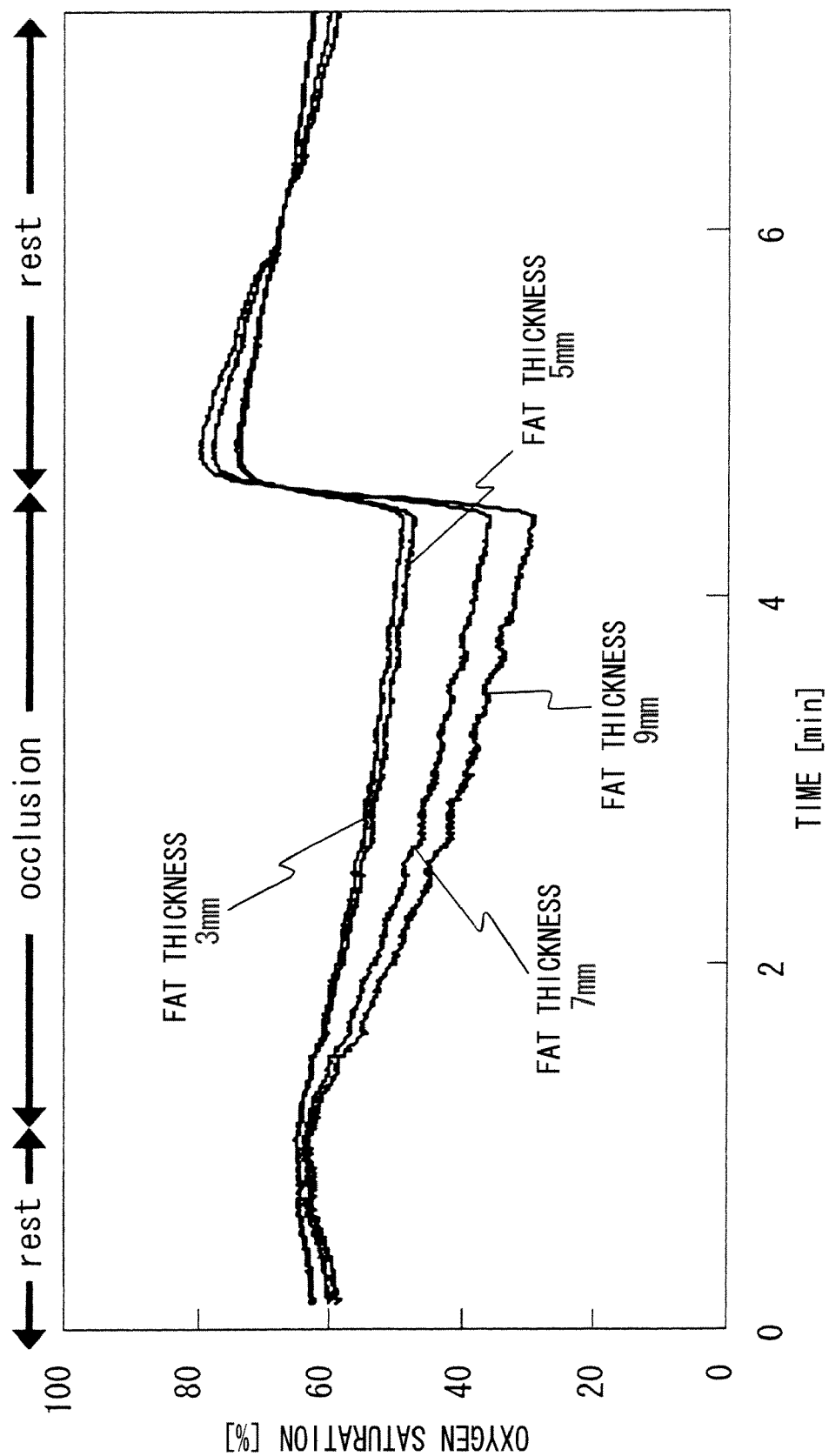
FIG. 9 is a diagrammatic view showing an oxygen saturation in each fat thickness.

FIG. 9 shows the result in which the oxygen saturation is actually measured in a region of the fat layer of 3 mm. As can be seen from FIG. 9, the use of the S-μa_m curve for the fat thickness (5 to 9 mm) which is different from the actual case generates the error up to about 30% in terms of the value of oxygen saturation $S_tO_2$. This is attributed to the fact that the shape of the S-μa_m curve is largely changed in accordance with the fat thickness.

In the spatially resolved method, it can be found that an accurate absolute value of the hemoglobin concentration is hardly obtained unless the scattering coefficient of the deep layer tissue is already known. On the other hand, the influence of the judgment of the scattering coefficient can largely be decreased in the case of the oxygen saturation $S_tO_2$. However, even in the oxygen saturation $S_tO_2$, because the fat thickness has a large influence, it is necessary that the fat thickness be previously recognized in the quantification.

From the result of the fat thickness of 3 mm and 5 mm shown in FIG. 9, when the fat thickness is measured with accuracy of about ±1%, it is estimated that the oxygen saturation $S_tO_2$ can be obtained with an error of 2 to 3% or less. Therefore, the fat thickness can be measured by the simple measuring method with a slide caliper or the like.

From the results of the simulation and the actual measurement, in the exemplary embodiment, the absorption coefficient μa_m of the muscle tissue is obtained in accordance with the fat thickness, and the hemoglobin concentration and the oxygen saturation are obtained from the absorption coefficient μa_m of the muscle tissue.

In Step 108, the absorption coefficient μa_m of the muscle tissue is obtained from the formula (2). That is, the constants a, b, and c corresponding to the fat thickness input in Step 102 are read from the memory 20, and the absorption coefficient μa_m of the muscle tissue is obtained from the constants a, b, and c and the spatial slope S obtained in Step 106 using the equation (2). The absorption coefficient μa_m of the muscle tissue is obtained in each wavelength. In the following description, it is assumed that $\mu\lambda^1\_am$ is an absorption coefficient of the muscle tissue in the case of the first wavelength λ1, and it is assumed that $\mu\lambda^2\_am$ is an absorption coefficient of the muscle tissue in the case of the second wavelength λ2. As described above, because the shape of the S-μa_m curve depends on the scattering coefficient μs_m of the muscle tissue, the absorption coefficient μa_m of the muscle tissue is obtained using the S-μa_m curve having the scattering coefficient μs_m of the muscle tissue of 0.8.

In Step 110, an oxygenated hemoglobin concentration [HbO$_2$] is obtained based on the absorption coefficients $\mu\lambda^1\_am$ and $\mu\lambda^2\_am$ of the muscle tissue obtained in Step 108. The oxygenated hemoglobin concentration [HbO$_2$] can be obtained from the following formula.

[Formula 3]

$$[HbO_2] = \frac{\varepsilon_{Hb}^{\lambda 2} \mu_{a\_m}^{\lambda 1} - \varepsilon_{Hb}^{\lambda 1} \mu_{a\_m}^{\lambda 2}}{\varepsilon_{HbO_2}^{\lambda 1} \varepsilon_{Hb}^{\lambda 2} - \varepsilon_{HbO_2}^{\lambda 2} \varepsilon_{Hb}^{\lambda 1}} \quad (3)$$

Here, $\varepsilon\lambda^1 Hb$ is a molecular extinction coefficient of the deoxygenated hemoglobin at the first wavelength $\lambda 1$, $\varepsilon\lambda^2 Hb$ is a molecular extinction coefficient of the deoxygenated hemoglobin at the second wavelength $\lambda 2$, $\varepsilon\lambda^1 HbO_2$ is a molecular extinction coefficient of the oxygenated hemoglobin at the first wavelength $\lambda 1$, and $\varepsilon\lambda^2 HbO_2$ is a molecular extinction coefficient of the oxygenated hemoglobin at the second wavelength $\lambda 2$. Known values are used as the molecular extinction coefficients $\varepsilon\lambda^1 Hb$, $\varepsilon\lambda^2 Hb$, $\varepsilon\lambda^1 HbO_2$, and $\varepsilon\lambda^2 HbO_2$ (for example, values described in Non-Patent Document 10).

In Step 112, a deoxygenated hemoglobin concentration [Hb] is obtained based on the absorption coefficients $\mu\lambda^1\_am$ and $\mu\lambda^2\_am$ of the muscle tissue obtained in Step 108. The deoxygenated hemoglobin concentration [Hb] can be obtained from the following formula.

[Formula 4]

$$[Hb] = \frac{\varepsilon_{HbO_2}^{\lambda 2} \mu_{am}^{\lambda 1} - \varepsilon_{HbO_2}^{\lambda 1} \mu_{a\_m}^{\lambda 2}}{\varepsilon_{HbO_2}^{\lambda 1} \varepsilon_{Hb}^{\lambda 2} - \varepsilon_{HbO_2}^{\lambda 2} \varepsilon_{Hb}^{\lambda 1}} \quad (4)$$

In Step 114, total hemoglobin [total Hb] is obtained by the following formula.

[total Hb]=[HbO$_2$]+[Hb]    (5)

In Step 116, the oxygen saturation S$_r$O$_2$ is obtained by the following formula.

[Hb]=[HbO$_2$]/[total Hb]    (5)

In Step 118, the output unit 22 supplies the obtained oxygenated hemoglobin concentration [HbO$_2$], deoxygenated hemoglobin concentration [Hb], and oxygen saturation S$_r$O$_2$.

Thus, in the exemplary embodiment, the absorption coefficient palm of the muscle tissue is obtained using the S-$\mu$a_m curve corresponding to the fat thickness, and the oxygenated hemoglobin concentration, deoxygenated hemoglobin concentration, and an oxygen saturation of the muscle tissue are obtained, based on the absorption coefficient $\mu$a_m of the muscle tissue. Therefore, the oxygenated hemoglobin concentration, the deoxygenated hemoglobin concentration, and the oxygen saturation can accurately be obtained while the influence of the fat thickness is corrected, and the quantitative performance can largely be improved for the oxygenated hemoglobin concentration, the deoxygenated hemoglobin concentration, and the oxygen saturation.

Although the hemoglobin concentration of the muscle tissue of the human arm is measured in the exemplary embodiment, the invention is not limited thereto. For example, the invention can be applied to an apparatus which measures a sugar content of fruity flesh of the fruits. In such cases, it is necessary that the wavelength of LED be set at a suitable value for measuring the absorption coefficient of glucose, and it is necessary that the distance between LED and PD be set at a distance suitable to thickness of an integument or an endodermis of the fruits. However, the sugar content of fruity flesh of the fruits can basically be measured by the similar technique. That is, the invention can be applied to other objects except for the living body as long as the light reaches an internal tissue.

In the exemplary embodiment, two PDs are provided. Alternatively, one PD and two LEDs may be provided. LED or PD may movably be provided, that is, the distance between LED and PD may be adjusted. In such cases, the distance between LED and PD is set at the first predetermined distance d1 to receive the light emitted from LED, and the distance between LED and PD is set at the second predetermined distance d2 to receive the light emitted from LED.

Figure 10:
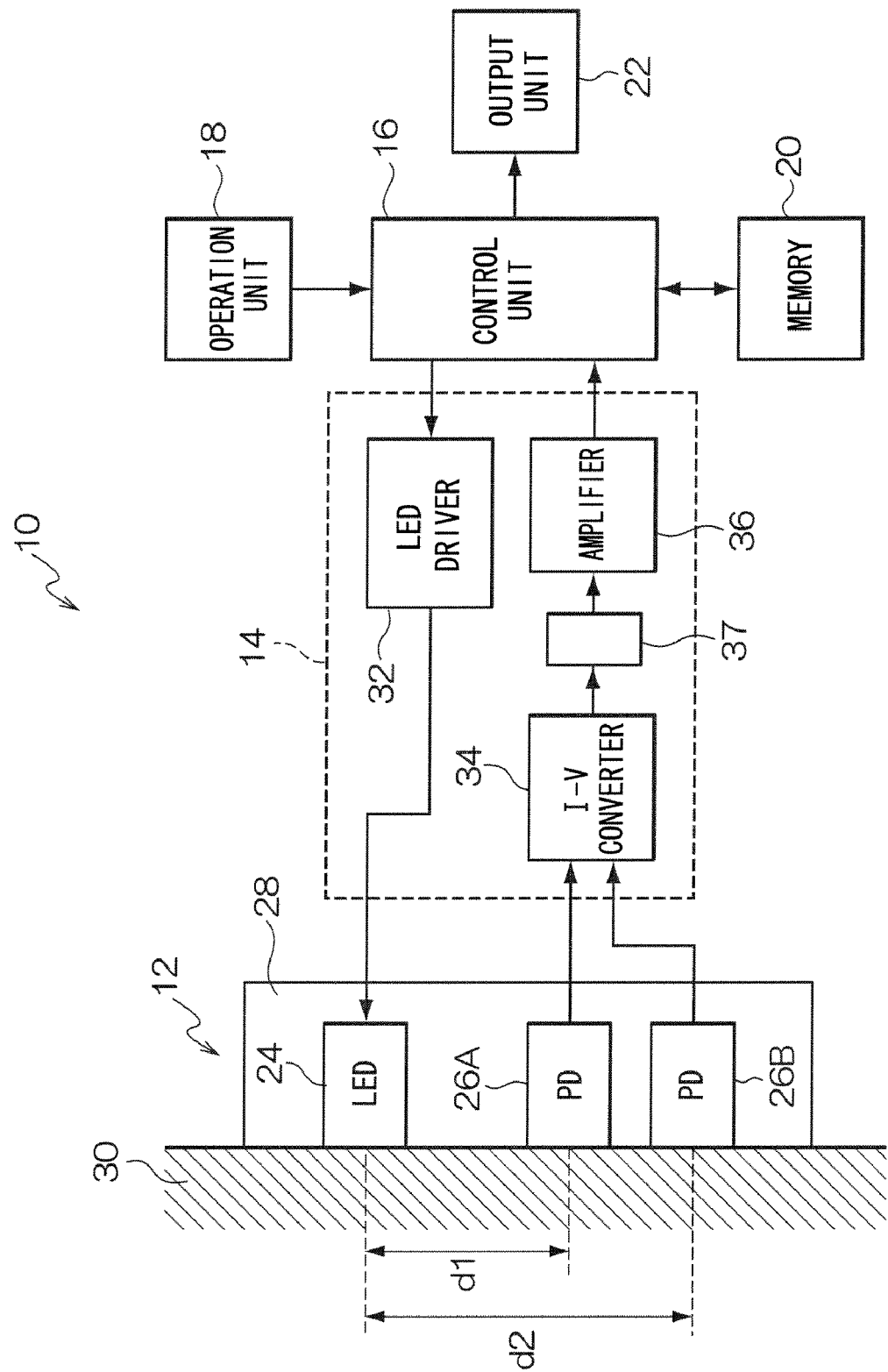
FIG. 10 is a schematic diagram showing another example of the optical measuring apparatus.

Alternatively, the light is emitted in a pulsed or intermittent manner with LED or the like, and sensitivity and accuracy of the output of the element such as PD which is of the light receiving means may be improved by adding a lock-in amplifier (or a boxcar integrator or a phase sensitive detector) 37 having a time resolved method to a preceding stage of the amplifier 36 as shown in FIG. 10. When two LEDs are provided, the light emission or a light emission pattern is mutually repeated. In order to remove an influence of ambient light such as fluorescent light during the measurement, the modulation can be performed at a frequency different from a commercial frequency by a sine-wave alternating current.

The invention claimed is:

1. An optical measuring apparatus comprising:
   a light emitter for irradiating with light a layered structure which is an object of measurement, the layered structure comprising a plurality of layers including at least a superficial layer and a deep layer;
   a light receiver for receiving, at a position at a first predetermined distance from the light emitter, light emitted from the light emitter and transmitted through the superficial layer and the deep layer, and for receiving, at a position at a second predetermined distance from the light emitter, light which is emitted from the light emitter and transmitted through the superficial layer and the deep layer and which has a deep layer transmission distance which is different from that of the light received at the position at the first predetermined distance from the light emitter;
   a spatial slope computation device for obtaining a spatial slope based on intensities of the light received at the position at the first predetermined distance from the light emitter and the light received at the position at the second predetermined distance from the light emitter;
   storage means in which a computation parameter for computing a degree of light absorption in the deep layer is stored for each superficial layer;
   an input device for inputting a thickness for each superficial layer; and
   computing means for reading a stored computation parameter corresponding to an input superficial layer thickness, and obtaining the degree of light absorption in the deep layer based on a quadratic function of the spatial slope including the read computation parameter.

2. The optical measuring apparatus of claim 1, wherein the layered structure is a part of a living body, the superficial layer is a fat tissue, and the deep layer is a muscle tissue.

3. The optical measuring apparatus of claim 2, wherein the computing means obtains at least one of an oxygenated hemoglobin concentration, a deoxygenated hemoglobin concentration, and an oxygen saturation, based on the degree of light absorption.

4. The optical measuring apparatus of claim 1, wherein the light receiver comprises a first light receiving unit, which is located at the first predetermined distance from the light emitter, and a second light receiving unit, which is located at the second predetermined distance from the light emitter.

5. The optical measuring apparatus of claim 2, wherein the light receiver comprises a first light receiving unit, which is located at the first predetermined distance from the light emitter, and a second light receiving unit, which is located at the second predetermined distance from the light emitter.

6. The optical measuring apparatus of claim 3, wherein the light receiver comprises a first light receiving unit, which is located at the first predetermined distance from the light emitter, and a second light receiving unit, which is located at the second predetermined distance from the light emitter.

7. An optical measuring method comprising:

irradiating with light a layered structure which is an object of measurement, the layered structure comprising a plurality of layers including at least a superficial layer and a deep layer;

receiving, at a position at a first predetermined distance from a light irradiation position, light of the irradiation light which has been transmitted through the superficial layer and the deep layer, and receiving, at a position at a second predetermined distance from the light irradiation position, light of the irradiation light which has been transmitted through the superficial layer and the deep layer and which has a deep layer transmission distance which is different from that of the light received at the position at the first predetermined distance from the light irradiation position;

obtaining a spatial slope based on intensities of the light received at the position at the first predetermined distance from the light irradiation position, the light received at the position at the second predetermined distance from the light irradiation position, the first predetermined distance, and the second predetermined distance;

inputting a thickness for each superficial layer; and reading a stored computation parameter corresponding to an input superficial layer thickness, where computation parameters for computing a degree of light absorption in the deep layer are stored for each superficial layer thickness in the storage device, and obtaining the degree of light absorption based on the read computation parameter and the spatial slope.

8. A non-transitory storage medium that stores an optical measuring program for causing a computer to execute processing, the processing including:

irradiating with light a layered structure which is an object of measurement, the layered structure comprising a plurality of layers, the plurality of layers including at least a superficial layer and a deep layer;

receiving, at a position at a first predetermined distance from a light irradiation position, light of the irradiation light which has been transmitted through the superficial layer and the deep layer, and receiving, at a position at a second predetermined distance from the light irradiation position, light of the irradiation light which has been transmitted through the superficial layer and the deep layer, and which has a deep layer transmission distance which is different from that of the light received at the position at the first predetermined distance from the light irradiation position;

obtaining a spatial slope based on intensities of the light received at the position at the first predetermined distance from the light irradiation position, the light received at the position at the second predetermined distance from the light irradiation position, the first predetermined distance, and the second predetermined distance;

inputting a thickness for each superficial layer; and reading a stored computation parameter corresponding to an input superficial layer thickness, where computation parameters for computing a degree of light absorption in the deep layer are stored for each superficial layer thickness in the storage device, and obtaining the degree of light absorption based on the read computation parameter and the spatial slope.

* * * * *